(12) United States Patent
Osborne et al.

(10) Patent No.: US 6,604,903 B2
(45) Date of Patent: Aug. 12, 2003

(54) AUTOMATED DRUG VIAL SAFETY CAP REMOVAL

(75) Inventors: Joel A. Osborne, Oklahoma City, OK (US); William C. Aven, Edmond, OK (US)

(73) Assignee: Forhealth Technologies, Inc., Oklahoma City, OK (US)

( * ) Notice: Subject to any disclaimer, the term of this patent is extended or adjusted under 35 U.S.C. 154(b) by 0 days.

(21) Appl. No.: 09/998,905

(22) Filed: Nov. 30, 2001

(65) Prior Publication Data
US 2003/0103839 A1 Jun. 5, 2003

(51) Int. Cl.⁷ .............................. B65B 43/26; B67B 7/00
(52) U.S. Cl. ........................ 414/411; 81/3.2; 81/3.07; 81/3.31; 81/3.55
(58) Field of Search ........................... 414/411; 81/3.2, 81/3.07, 3.55, 3.31; 53/381.4

(56) References Cited

U.S. PATENT DOCUMENTS

| | | | | |
|---|---|---|---|---|
| 3,848,485 A | * | 11/1974 | Grenci ........................ 81/57.11 |
| 4,773,285 A | * | 9/1988 | Dionne ........................ 81/3.2 |
| 5,040,437 A | * | 8/1991 | Mueller ........................ 81/3.2 |
| 5,735,181 A | * | 4/1998 | Anderson .................... 81/3.25 |
| 5,805,454 A | | 9/1998 | Valerino, Sr. et al. |
| 5,826,409 A | * | 10/1998 | Slepicka et al. .............. 53/492 |
| 6,048,086 A | | 4/2000 | Valerino, Sr. |
| 6,142,039 A | * | 11/2000 | Herring, Sr. .................. 81/3.2 |
| 2002/0020459 A1 | | 2/2002 | Baldwin et al. |

* cited by examiner

Primary Examiner—Steven A. Bratlie
(74) Attorney, Agent, or Firm—Darby & Darby

(57) ABSTRACT

The present invention provides an automated safety cap removal mechanism for an automated medication preparation system. The mechanism includes an automated gripping device for securely holding and transporting a vial containing the medication to and from a first station and a cap removal device for removing a safety cap of the vial in a just-in-time for use manner. The cap removal device being located at the first station. By providing a just-in-time for use safety cap removal mechanism, the labor intensive task of removing safety caps can be incorporated into an automated medication preparation system.

47 Claims, 8 Drawing Sheets

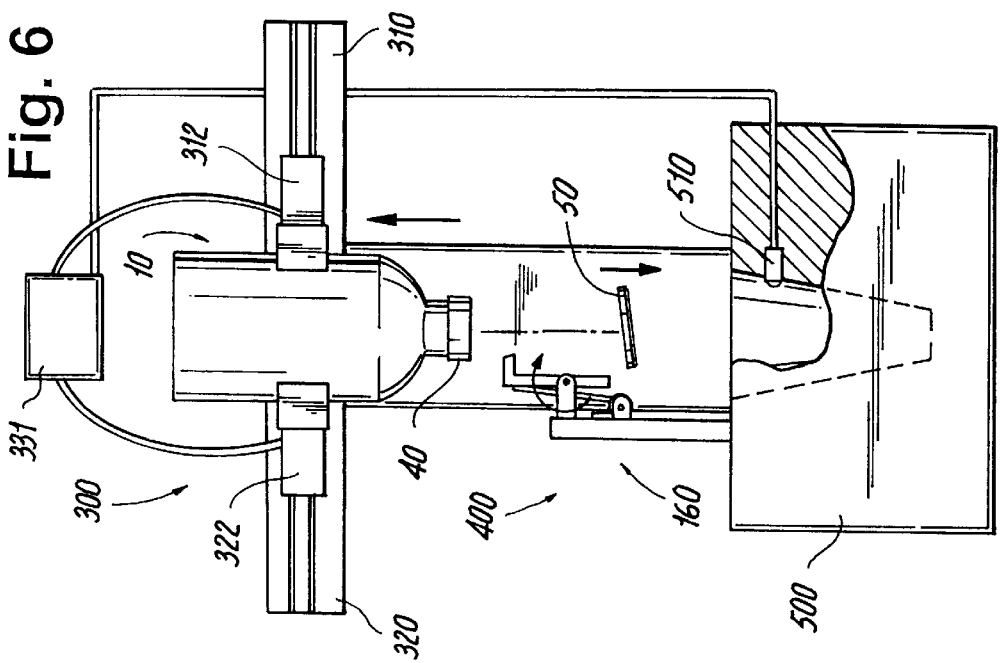

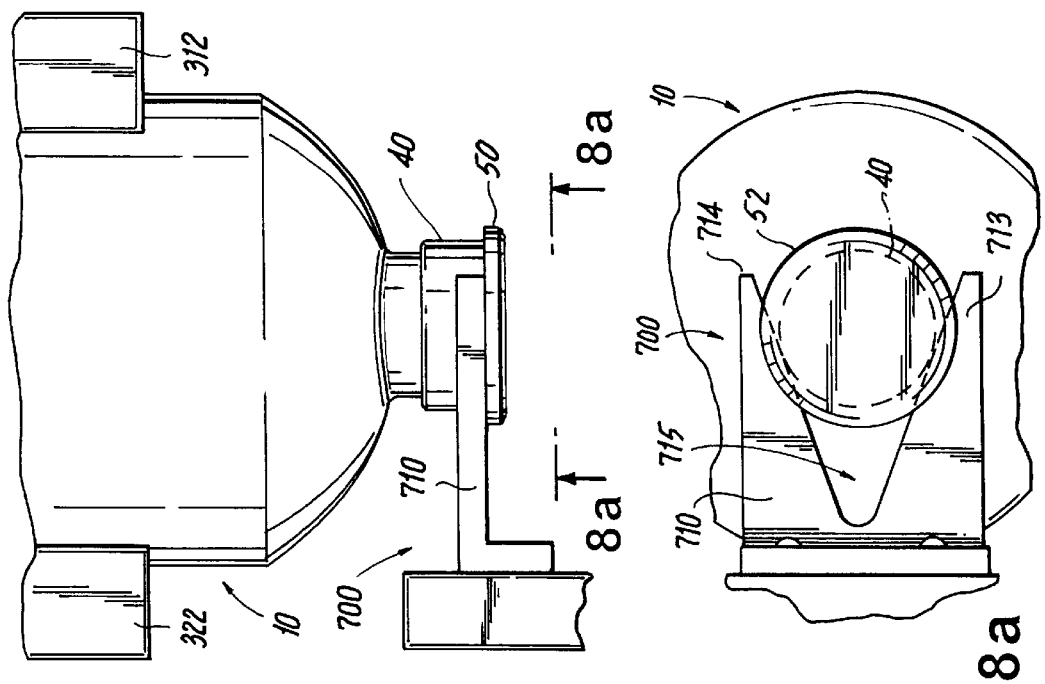
Fig. 8
Fig. 8a
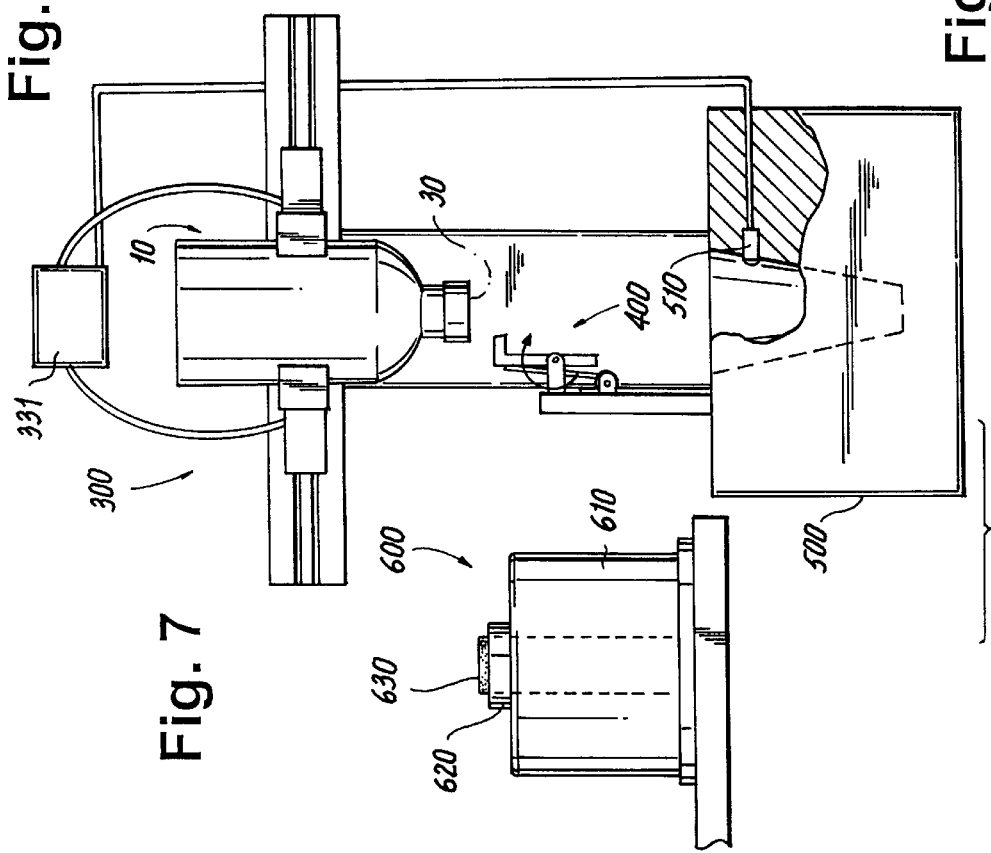
Fig. 7

Fig. 9
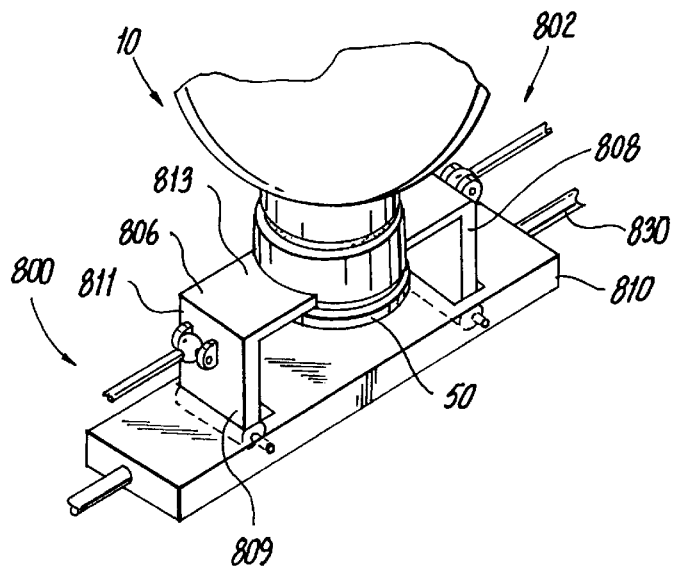
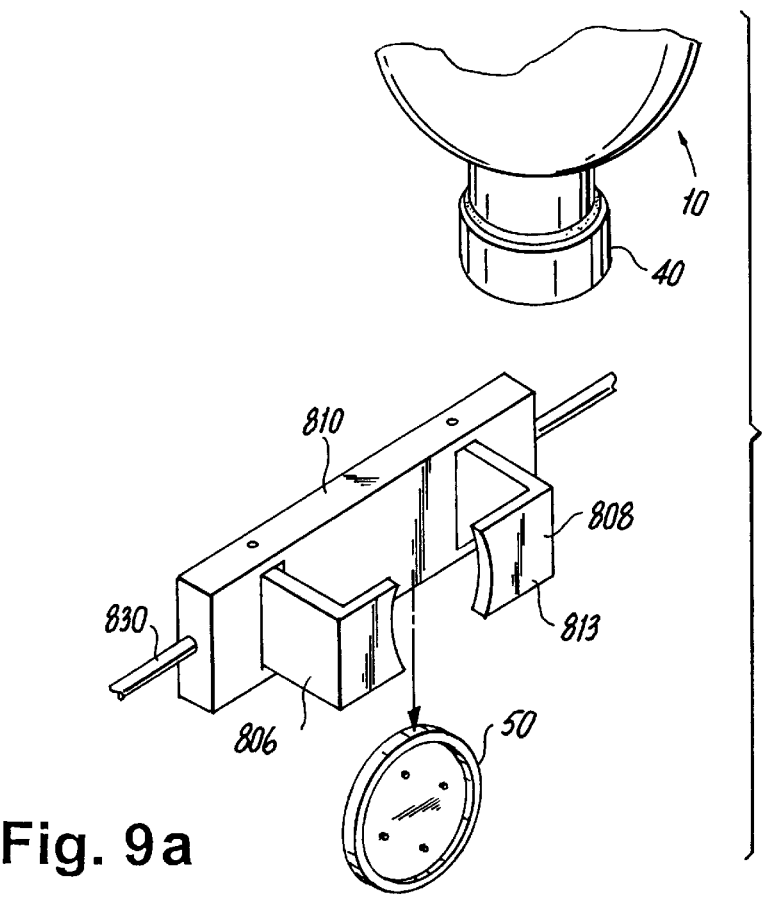
Fig. 9a

AUTOMATED DRUG VIAL SAFETY CAP REMOVAL

FIELD OF THE INVENTION

The present invention relates generally to medical equipment, and more particularly, to an automated apparatus for filling unit dose, disposable syringes with one or more medications that are each stored in a vial.

BACKGROUND OF THE INVENTION

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, including a large number of doses of medications have to be prepared daily. Traditionally, these doses have been prepared manually in what is an exacting but tedious responsibility for a highly skilled staff. In order to be valuable, automated systems must maintain the exacting standards set by medical regulatory bodies, while at the same time simplifying the overall process and reducing the time necessary for preparing the medications.

Because syringes are often used as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a sealed vial. As shown in FIGS. 1 and 1a, a conventional vial 10 is formed of a body 20 (i.e., glass) and is sealed with a membrane (septum) 30 across the open end 22 of the body 20. The membrane 30 can be formed of any type of material that is typically used in this setting for sealing a container (e.g., vial 10) yet at the same time permit a user to puncture or pierce the membrane 30 with an instrument to gain access to the inside of the container. In one exemplary embodiment, the membrane 30 is formed of a rubber material that can be easily stretched across the open end 22 while still providing the necessary seal.

The membrane 30 is securely held in place across the open end 22 by a retainer ring 40 that is itself securely attached to the body 20. The retainer ring 40 circumferentially surrounds a neck 21 formed at the open end 22 and includes an upper section 42 that seats against an upper surface the membrane 30 and a lower section 44 that engages the body 20 underneath the neck 21. The retainer ring 40 is open in a middle section 23 thereof such that when the retainer ring 40 is securely attached to the body 20, the retainer ring 40 holds the stretched membrane 30 in place with the membrane 30 being visible in the open middle section of the retainer ring 40. The retainer ring 40 can be attached to the body 20 using any number of conventional techniques, including a crimping process, so long as the retainer ring 40 securely holds the membrane 30 such that a seal results between the open end 22 and the membrane 30.

A safety cap 50 is securely attached to the vial 10 to cover the exposed membrane 30 and further seal the open end 22 of the vial body 20. The safety cap 50 is typically formed of a light, disposable material, such as a plastic, and is attached at the end 22 in a tamper proof manner. For example, the safety cap 50 is attached so that once it is removed, it can not be reattached to the vial body 22. Thus, a vial that does not contain a safety cap 50 is easily recognizable and indicates that either (1) the safety cap 50 has previously been removed and medication in the vial 20 has been withdrawn, (2) the safety cap 50 was not properly attached and has accidently become displaced, (3) the vial 50 has been tampered with, etc. In any event and unless the exact history of the particular vial is know, any vial that is missing a safety cap 50 is ordinarily discarded and not used.

The safety cap 50 is a solid member that extends completely across the exposed portion of the membrane 30 and, preferably, the peripheral edges of the safety cap 50 are downwardly curved so that the peripheral edges overlap the outer peripheral edges of the retainer ring 40. The safety cap 50 contains features that permit it to be attached to the retainer ring 40. In one exemplary embodiment, the retainer ring 40 has a plurality of bosses 60 that extends upwardly from the retainer ring 40 near the inner edge of the retainer ring 40. When the safety cap 50 is attached to the retainer ring 40, the plurality of bosses 60 seats within complementary openings formed in the safety cap 50 so as to frictionally couple the two parts together. For example, the safety cap 50 can be injected molded around the retainer ring 40, thereby resulting in the formation of the safety cap 50 around the plurality of bosses 60. The connection between the bosses 60 and the safety cap 50 represents a weakened section which breaks when force is applied to the safety cap 50 in an appropriate direction. This results in the safety cap 50 being easily removed, while at the same time provides a tamper proof arrangement because, once the weakened section is broken and the safety cap 50 is free, the safety cap 50 can not later be reattached to the retainer ring 40 or any other part of the vial 10.

It will be understood that the parts of the vial 10 of FIGS. 1 and 1a are merely exemplary in nature and the many different tamper proof vial constructions are available. The common elements are that the vials each contain a membrane and the safety cap is easily removable but at the same time provides further protection of the membrane and also serves as an indicator of whether the vial has been used.

In conventional medication preparation, a trained person retrieves the correct vial from a storage cabinet or the like, confirms the contents and then removes the safety cap manually. This is typically done by simply popping the safety cap off with ones hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe. Often, the membrane is first pierced with an instrument for injecting a diluent into the medication prior to withdrawal of the medication. This is a very time and labor intensive task and what is needed in the art and has heretofore not been available is a system and method for automating the medication preparation process and more specifically, an automated system and method for retrieving a drug vial, removing the safety cap, and cleaning the vial just prior to use.

SUMMARY OF THE INVENTION

The present invention provides an automated safety cap removal mechanism for an automated medication preparation system. The mechanism includes an automated gripping device for securely holding and transporting a vial containing the medication to and from a first station and a cap removal device for removing a safety cap of the vial in a just-in-time for use manner. The cap removal device being located at the first station. By providing a just-in-time for use safety cap removal mechanism, the labor intensive task of removing safety caps can be incorporated into an automated medication preparation system.

In one embodiment, the cap removal device includes a support member and a pivotable member coupled to the support member. The pivotable member is biased in a first direction such that when the automated gripping device delivers the vial to the first station, the pivotable member engages the safety cap which is then removed from the vial by moving the vial in a second direction as it is held by the automated gripping device. The pivotable member thus acts as a pry bar to cause removal of the safety cap.

In another embodiment, the cap removal device includes a wedge element for reception between the safety cap and a body of the vial such that when the automated gripping device delivers the vial to the first station, the wedge element is received between the safety cap and the vial body. The safety cap is then removed from the vial by moving the vial in a second direction as it is held by the automated gripping device.

In yet another embodiment, the cap removal device includes a rotatable member having first and second gripping sections. Each of the first and second gripping sections has openable and closeable decapper elements that are controlled by a control unit. The safety cap is removed by disposing the safety cap between the opened decapper elements which are then closed prior to moving the vial in a second direction as the safety cap is gripped by the decapper elements. This results in the safety cap being removed.

In another aspect, the mechanism includes a detector (e.g., a sensor) for sensing the removal of the safety cap from the vial. The detector is in communication with a control unit that also communicates with the automated gripping device for moving the automated gripping device to select locations. The detector generates a detection signal upon sensing that the safety cap has been removed. This detection signal instructs the control unit to proceed with moving the decapped vial to either a next station or to a location where a next operation is performed.

The present application also provides a method for just-in-time removal of a safety cap from a drug vial. The method includes the steps of first moving the drug vial onto a deck of an automated medication preparation system. The drug vial has the safety cap affixed over an opening thereof. Second, the drug vial is gripped against movement, and third a step is performed for removing the safety cap while gripping the drug vial.

Further aspects and features of the exemplary automated safety cap removal mechanism disclosed herein can be appreciated from the appended Figures and accompanying written description.

BRIEF DESCRIPTION OF THE DRAWINGS

FIG. 5 is a side elevational view of a safety cap removal device used in combination with the automated gripping device of FIG. 3 for removing the safety cap from the vial, the vial being shown in a first position prior to removal of the safety cap;

FIG. 6 is a side elevational view of the safety cap removal device of FIG. 5 used in combination with a chute and a detector for sensing the removal of the safety cap;

FIG. 7 is a side elevational view of the safety cap removal device and automated gripping device of FIG. 5 shown in a second position where the safety cap has been removed and the vial is ready for contacting a cleaning surface;

FIG. 8 is a side elevational view of an exemplary safety cap removal device according to another embodiment;

FIG. 8a is a bottom plan view of a portion of the safety cap removal device of FIG. 8;

FIG. 9 is a perspective view of yet another embodiment of an exemplary safety cap removal device in a first closed position;

FIG. 9a is a perspective view of the safety cap removal device of FIG. 9 in a second open position;

DETAILED DESCRIPTION OF A PREFERRED EMBODIMENT

Figure 1:
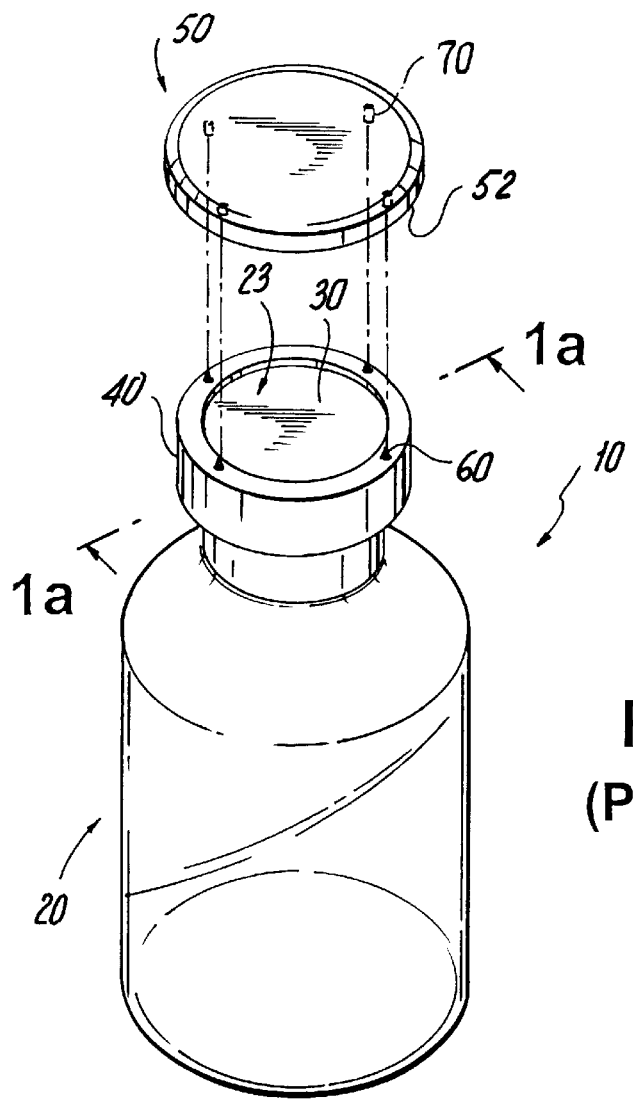
FIG. 1 is a partially exploded perspective view of a conventional vial having a safety cap exploded therefrom.
Figure 1A:
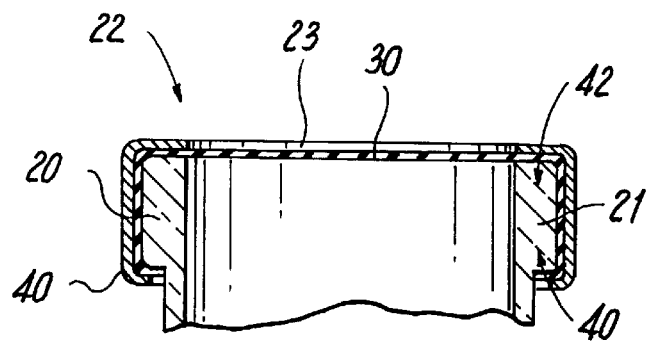
FIG. 1a is a partial cross-sectional side elevational view of the conventional vial of FIG. 1 with the safety cap being removed.
Figure 2:
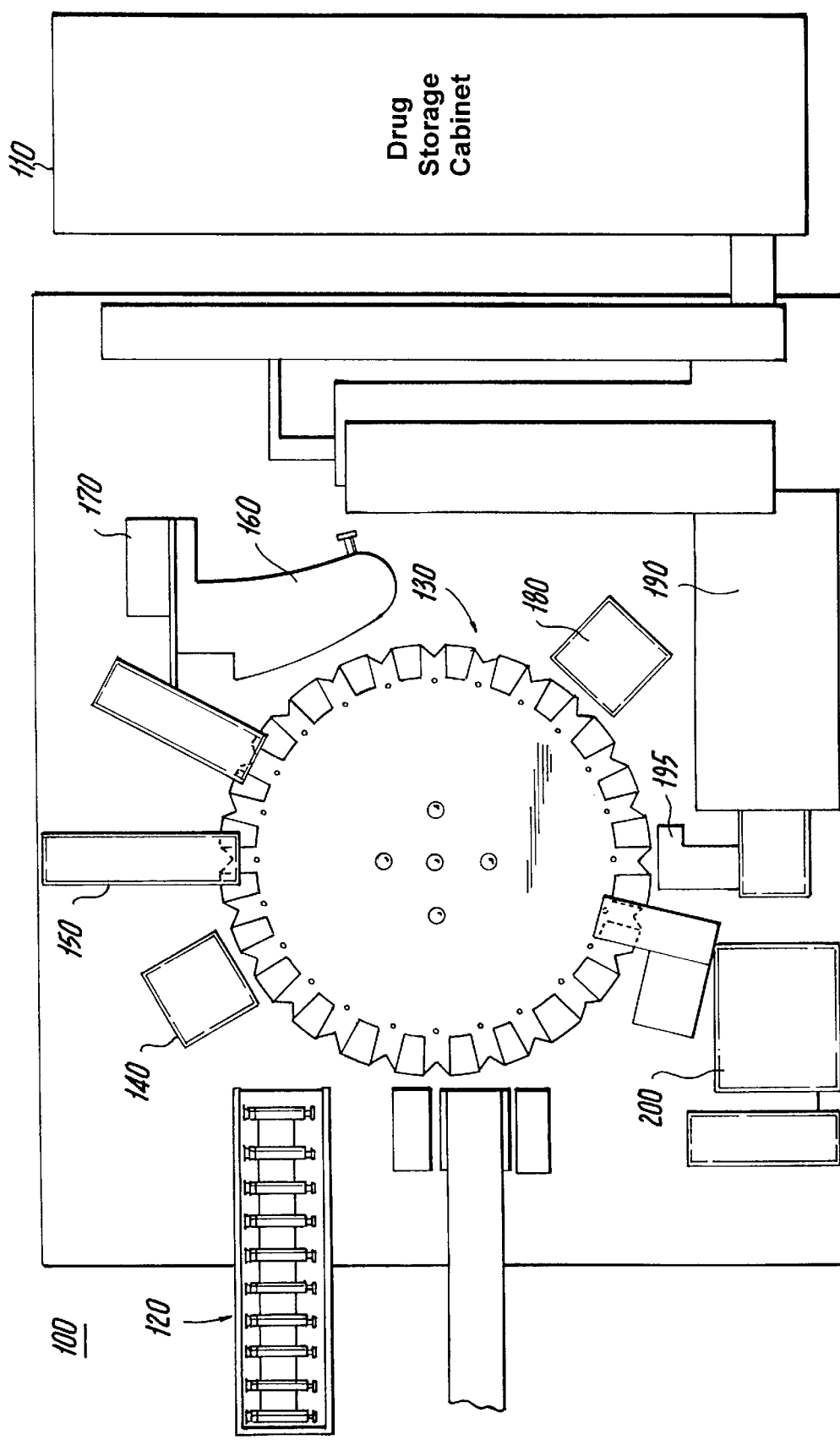
FIG. 2 is a schematic diagram of an automated system for preparing a medication to be administered to a patient.

FIG. 2 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc. under proper storage conditions. Typically, medications and the like are stored in sealed containers, such as vials 10 of FIG. 1, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at the first station 110 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150. At this point, the syringe is ready for use.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to a fourth station 160 using an automated mechanism, such a robotic gripping device as will be described in greater detail. At the fourth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station 170 for injecting a diluent into the medication contained in the sealed container and then subsequently mixing the medication and the diluent to form the medication composition that is to be disposed into the prepared syringe. At a fluid transfer station, the prepared medication composition is withdrawn from the container (i.e., vial) and is then disposed into the syringe. For example, a cannula can be inserted into the sealed vial and the medication composition then aspirated into a cannula set. The cannula is then withdrawn from the vial and positioned using the rotary apparatus 130 in line with (above, below, etc.) the syringe. The unit dose of the medication composition is then delivered to the syringe, as well as additional diluent if necessary or desired. The tip cap is then placed back on the syringe at a sixth station 180. A seventh station 190 prints and applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 195 located prior to the unloading station 200.

FIGS. 3 through 7 illustrate parts of the first station 110 and the fourth station 160 (FIG. 2) and, more specifically, an automated device for delivering a sealed vial from the first station 110 to the fourth station 160 is illustrated as well as the various components of the fourth station 160 for removing the safety cap and cleaning the exposed end of the vial 10.

Figures 3, 4:
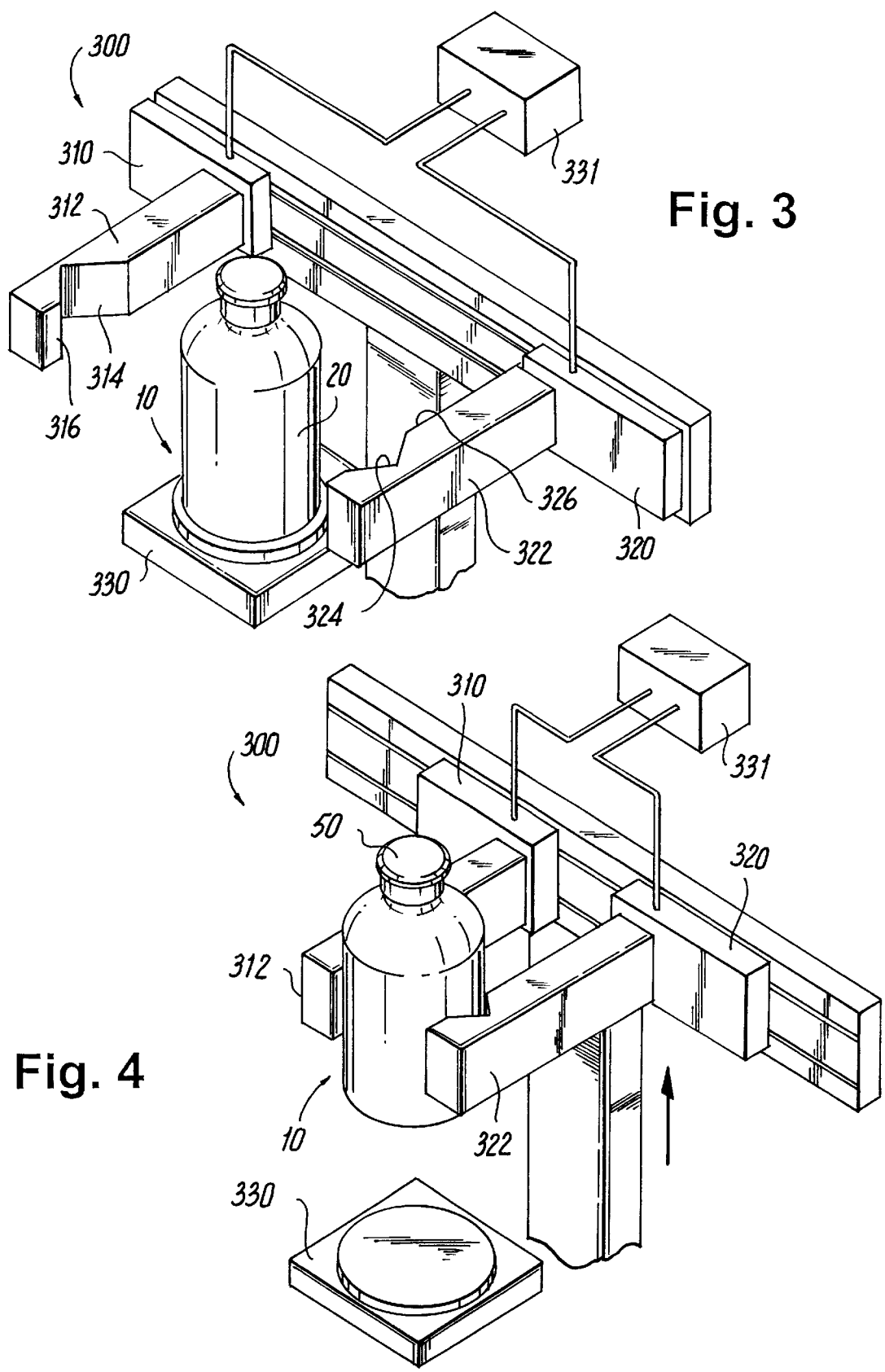
FIG. 3 is a perspective view of an automated device for gripping and transporting the vial of FIG. 1 to and from various stations of the automated medication preparation system of FIG. 2, the automated gripping device being shown in a first open position.
FIG. 4 is a perspective view of the automated gripping device of FIG. 3 shown in a second closed position in which the vial of FIG. 1 is securely held thereby and lifted upwardly from a pedestal.

FIG. 3 is a perspective view of an automated device 300 for gripping and transporting the vial 10 to and from various stations of the automated medication preparation system 100 (FIG. 2). The device 300 is a controllable device that is operatively connected to a control unit, such as a computer, which drives the device 300 to specific locations of the system 100 at selected times. The control unit can be a personal computer that runs one or more programs to ensure coordinated operation of all of the components of the system 100.

In one exemplary embodiment, the automated device 300 is a robotic device and preferably, the automated device 300 is a linear actuator with a gripper. The device 300 has first and second positionable gripping arms 310, 320 which are adjustable in at least several directions. For example, each of gripping arms 310, 320 has fully independent reach (y axis) and vertical axes (x axis) which provide the flexibility and motion control that is desirable in the present system 100 (FIG. 2). The gripping arms 310, 320 are programed to work together in tandem so that both arms 310, 320 are driven to the same location at the same time.

The gripping arm 310 includes a gripper section 312 that is in the form of an elongated member that extends outwardly from the rest of the gripping arm 310. The gripper section 312 is contoured to seat against a portion of the vial 10 and because the vial body 20 is typically circular in shape, the gripper section 312 includes an arcuate recess 314 with planar sections 316 on either side of the arcuate recess 314. The arcuate recess 314 has a complementary shape as the shape of the body 20 so that the body 20 conveniently nests within the recess 314. Similarly, the gripping arm 320 includes a gripper section 322 that can be contoured to seat against a portion of the vial 10 and also cooperate with the gripper section 312 so as to grippingly hold the vial 10 between the gripper sections 312, 322. The gripper section 322 can include an arcuate recess 324 with planar sections 326 on either side of the arcuate recess 324.

In FIG. 3, a first open position of the gripping arms 310, 320 is illustrated with the gripping sections 312, 322 being spaced sufficiently from one another so as to permit the vial 10 to be freely disposed between the gripping sections 312, 322. The vial 10 rests upon a pedestal 330 or the like after having been removed from the station 110 (FIG. 1) and after other system operations have been performed. For example, before the vial 10 is disposed on the pedestal 330, the label (not shown) on the vial 10 is read by one of the readers of the system 100 to ensure that the proper medication has been removed from the station 110. The vial 10 is then placed on the pedestal 330 using conventional techniques, such as using a conveyor, gripping actuators, etc. The vial 10 is placed in an upright position on the pedestal 330.

Using a control unit 331 (e.g., programmable actuator, microprocessor, etc.), the gripping arms 310, 320 are driven to the first position shown in FIG. 3. An actuator or the like of the device 300 is then activated causing the gripping arms 310, 320 to move inwardly toward one another. The vial body 20 is aligned with the gripping sections 312, 322 such that as the gripping arms 310, 320 move toward one another, the vial body 20 seats within the arcuate recesses 314, 324 of the gripping sections 312, 322. The gripping sections 312, 322 engage the vial body 20 below the neck portion thereof. The gripping arms 310, 320 are driven to a second closed position illustrated in FIG. 4 where the vial 10 is securely held and retained between the gripping arms 310, 320 to permit the vial 10 to be transported to another station or location of the system 100.

The control unit 331 can be designed so that the user inputs the size and type of vial 10 that is being used and based on this information, the control unit will direct the gripping arms 310, 320 to be driven a predetermined distance toward one another. The predetermined distance is a distance that ensures that the vial body 20 is securely gripped between the gripping arms 310, 320 without damaging the vial body 20 due to excessive pressure being applied by the gripping arms 310, 320 against the vial body 20. The control unit 331 can be remote from the system 100 and can communicate using any number of conventional techniques, including wireless communication.

Sensors, i.e. pressure sensors, (not shown) may be incorporated into the gripping sections 312, 322 to facilitate the gripping sections 312, 322 being driven into appropriate locations to ensure that the vial body 20 is securely held therebetween while preventing excessive pressure from being applied on the vial body 20 by the gripping sections 312, 322.

In FIG. 4, the gripping arms 310, 320 have been driven in the vertical direction (x axis), after the vial body 20 is securely held between the gripping sections 312, 322, resulting in the vial body 20 being raised off of the pedestal 330. As previously-mentioned, the device 300 is a fully programable device and the gripping arms 310, 320 are configured to move in several directions. For example, after the vial body 20 has been raised off of the pedestal 330, as shown in FIG. 4, the gripping arms 310, 320 are actuated and rotated so that the vial body 20 assumes an inverted position (e.g., see FIG. 5). In this inverted position, the safety cap 50 of the vial 10 faces downward.

The control unit then drives the device 300 to the station 160 (FIG. 2) and more specifically, the inverted vial 10 is driven to the station 160 so that additional operations can be performed on the vial 10. As shown in FIG. 5, one of the operations performed at the station 160 is that the safety cap 50 is removed from the vial 10. While the station 160 is "the fourth station" referred to in the discussion of FIG. 1, it is the "first station" at which cap removal takes place.

Cap removal mechanism 400 includes a support member 410 and a pivotable member 430 that engages and removes the safety cap 50. The support member 410 is an upstanding member that has a first face 412 and an opposing second face 414 that faces the inverted vial 10 as the vial 10 is driven toward the mechanism 400. Extending outwardly from the second face 414 are a pair of spaced arms 416 that terminate in distal ends 418. Each arm 416 has an opening 420 formed therein near the distal end 418. The openings 420 are axially aligned with one another and act as pivot points for the pivotable member 430. The pivotable member 430 in this embodiment is generally in the form of a pry bar that is biased such that an upper end 432 thereof is biased in a direction away from the second face 414. Biasing element 440 provides the biasing force and in this embodiment, biasing element 440 is a spring operatively connected to the pivotable member 430 and the support member 410. In the biased rest position, the pivotable member 430 assumes a slanted orientation with a lower end 434 thereof being close to the second face 414 and the upper end 432 being located farther away from the second face 414.

The pivotable member 430 has a body with a flange 450 being formed and extending outwardly from the upper end 432. The flange 450 acts as a pry bar for engaging and removing the safety cap 50 as will be described in greater detail. The flange 450 extends from the upper end 432 at an angle so as to provide a gripping edge for engaging a bottom underneath section of the safety cap 50. The pivotable member 430 is pivotably attached to the support member 410 by any suitable means. For example, the pivotable member 430 can have protrusions that extend outwardly therefrom and are received in the openings 420 of the support member 410 to permit pivoting of the member 430. Alternatively, the pivotable member 430 can have axially aligned openings that receive a transverse member, such as a pin or the like, that extends through the openings 420 formed in the support member 410. In both of these embodiments and in other alternative embodiments, the pivotable member 430 is biased forward and at the same time pivotable about the support member 410.

The automated device 300 is programmed so that the vial 10, more specifically the safety cap 50 thereof, is properly aligned with the biased pivotable member 430 as the vial 10 is driven into contact with the pivotable member 430. The forward biased pivotable member 430 is positioned so that when the vial 10 is driven into contact with the pivotable member 430, the flange 450 engages a bottom underneath section 52 of the safety cap 50. The vial 10 is directed further toward the support member 410 and the flange 450 further retainingly seats against the bottom underneath section 52 of the safety cap 50 due to the forward bias force of the pivotable member 430 which causes a biasing force to be applied to the bottom underneath section 52 of the safety cap 50.

Once the pivotable member 430 engages the bottom underneath section 52 of the safety cap 50, the gripping arms 310, 320 are moved upwardly. Because the flange 450 is seated against the safety cap 50 in a biased manner, the upward movement of the gripping arms 310, 320 causes the safety cap 50 to become dislodged from the vial 10 as shown in FIG. 6. More specifically, the attachment between the safety cap 50 and the other elements that act to seal the vial 10 is broken. In the embodiment of FIG. 1, the safety cap 50 is broken away from the retainer ring 40 (FIG. 1) at the weakened section.

The station 160 also preferably includes a detector for sensing that the safety cap 50 has been removed from the vial 10 by the cap removal mechanism 400. As illustrated in FIG. 6, once the safety cap 50 has been removed, the safety cap 50 falls by gravity into a chute (hopper) 500, or the like, that is disposed below the cap removal mechanism 400. Within the chute 500 or in a location proximate thereto, a sensor 510 is disposed for detecting the falling safety cap 50. The sensor 510 can be any number of sensors that are configured to detect an object. For example, the sensor 510 may be an infrared based sensor that sends a detection signal once an object (the safety cap 50) crosses or otherwise interferes with the infrared beam, the sensor 510 generates the detection signal that is sent to the control unit or a microprocessor 331 associated with some other control mechanism of the system 100. The sensor 510 can also be a motion detector that is capable of detecting the falling safety cap 50.

The control unit 331 (microprocessor) is a programmable unit that is run with software and is configured so that the sensor 510 acts a safety mechanism in that if the sensor 510 does not generate the detection signal, the control unit will not advance the automated device 300 to the next station. Instead, the control unit will instruct the automated device to repeat the cap removal process. The vial 10, held between the gripping arms 310, 320 is returned to a location proximate to the cap removal mechanism 400 (unless the vial is there already) and the gripping arms 310, 320 are driven toward the pivotable member 430 again. The process is repeated with the gripping arms 310, 320 being moved upwardly.

In one embodiment, the control system is configured so that the cap removal process is repeated three separate times if the sensor 510 does not detect that the safety cap 50 has been removed and has fallen into the chute 500. In this situation, the automated device 300 is not further advanced to the next station; but instead, the system 100 is stopped and an error message is preferably generated and directs the user to manually inspect the vial 10 that is grasped between the gripping arms 310, 320. Alternatively, in the case that the sensor 510 does not detect the safety cap 50 after several attempts, the vial 10 grasped between the gripping arms 310, 320 is rejected and discarded and the system 100 continues with another vial 10 being selected from the station 110 where the drug vials 10 are stored.

When the safety cap 50 is properly removed, the detection signal is generated and delivered to the control unit which in turn instructs the automated device 300 to continue to the next station or next operation.

FIG. 7 illustrates the automated device 300 continuing to the next operation after the safety cap (not shown) has been properly removed by the cap removal mechanism 400. A cleaning device 600 is provided for cleaning the vial 10 after the safety cap has been removed. The cleaning device 600 includes a container 610 that holds a cleaning solution, such as an alcohol solution. A cap 620 closes the container 610 and a wick 630 or the like is used to supply the cleaning solution to the vial 10. The wick 630 has one end that is submersed in the cleaning solution and an opposite end that extends through the cap 620 and is available for contact with the vial 10. The end of the wick 630 that extends through the cap 620 is wetted with the cleaning solution.

The automated device 300 is moved so as to place the vial 10 into contact with the wick 630. More specifically, the membrane 30 (FIG. 1) is cleaned with the cleaning solution by contacting the membrane 30 with the wick 630. Preferably, the membrane 30 is cleaned by running the vial 10 across the wick 630 several times. By running the vial 10 back and forth across the wick 630, the membrane 30 is cleaned with the cleaning solution.

Once the membrane 30 is sufficiently cleaned, the vial 10 is then delivered to the next station, where the medication stored in the vial 10 is further processed. For example, a diluent can be injected into the vial 10 for preparing a medication solution after the medication (e.g., a powder) is mixed with the diluent.

FIGS. 8 and 8a illustrates another exemplary cap removal mechanism 700. The cap removal mechanism 700 includes a wedge or fork member 710 having spaced fingers or wedge elements 712, 713 that define a space 715. The vial 10 is disposed within the space 715 so that the underneath surface 52 of the safety cap 50 seats against the wedge 710. The wedge elements 712, 713 terminate in ends 714. The wedge elements 712, 713 capture and hold the safety cap 50, while permitting the vial body to be moved in an upward direction, thereby causing the dislodgement of the safety cap 50.

The removal of the safety cap 50 with the cap removal mechanism 700 is similar to the removal that occurs with the cap removal mechanism 400 in that the automated device 300 is brought into position relative to the cap removal mechanism 700 causing the vial 10 to become lodged within the space 715. Once the safety cap 50 is wedged between the elements 712, 713, the automated device 300 is then moved upwardly causing the safety cap 50 to become dislodged. The safety cap 50 falls into the chute 500 (FIG. 7) where the sensor 510 (FIG. 7) detects its presence and signals the control unit or like that the safety cap 50 was removed during the cap removal operation. If no safety cap 50 is detected, then the process is repeated as mentioned hereinbefore and if a predetermined number of attempts, no cap is sensed as being removed, the system 100 is stopped or alternatively, the vial 10 is rejected and the process continued.

FIGS. 9 and 9a illustrate yet another exemplary cap removal mechanism 800. In this embodiment, the cap removal mechanism 800 is a claw-like structure that includes a first gripping member 802. The cap removal mechanism 800 is rotatable so that the position of the first gripping member 802 can easily be changed. The first gripping member 802 has first and second spaced elements 806, 808 that are movable relative to one another and more specifically, are part of an automated device that is programmable to cause the opening and closing of the first and second spaced elements 806, 808. Each of the first and second elements 806, 808 has a first end 809 that is coupled to a base 810 and an opposing second end 811 that includes a flange 813. In the illustrated embodiment, the flange 813 is bent at a 90° angle relative to the other portion of the element. The first and second elements 806, 808 can be opened and closed using conventional actuator type mechanisms, e.g., piston operated system where linkage is connected thereto.

A shaft 830 extends outwardly from the base 810. The shaft 830 is part of the automated device that is configured to rotate the first gripping member 802. The rotation of the first gripping member 802 permits the first gripping member 802 to be inverted and face away from the vial 10.

FIG. 9 illustrates a first position in which the first gripping member 802 is located in an upper position facing the safety cap 50. In the first position, the first and second elements 806, 808 are closed with the safety cap 50 being disposed and securely held between the flanges 813. The first and second elements 806, 808 can be closed by actuating the automated device, as by the control unit or the like. When the first and second elements 806, 808 close, the flanges 813 are disposed above the safety cap 50 and then the automated device 300 is actuated and moves upwardly in a direction away from the first gripping member 802. Because the flanges 813 are seated above the safety cap 50, the flanges 813 prevent the safety cap 50 from moving upward. This restriction causes the safety cap 50 to become dislodged as the vial 10 is moved upward. The dislodged safety cap 50 is held between the flanges 813 as the vial 10 moves thereaway.

The automated device is actuated so that the first gripping member 802 is moved to a second position, shown in FIG. 9a. When the first gripping member 802 assumes the second lower position, the first and second elements 806, 808 are opened and the safety cap 50 that was held between the flanges 813 falls into the chute 500 (FIG. 7) where the sensor 510 (FIG. 7) is located to sense the passage of the safety cap 50 into and through the chute 500. As with the other embodiments, if the sensor 510 does not sense the passage of the safety cap 50 into the chute 500, the cap removal process is repeated using now the second gripping member 804, as it has assumed the first upper position facing the vial 10. If the safety cap 50 is not detected by the sensor 510 after several attempts, either the system 100 is stopped or the vial 10 is rejected and a next vial 10 is brought into position.

Figure 9B:
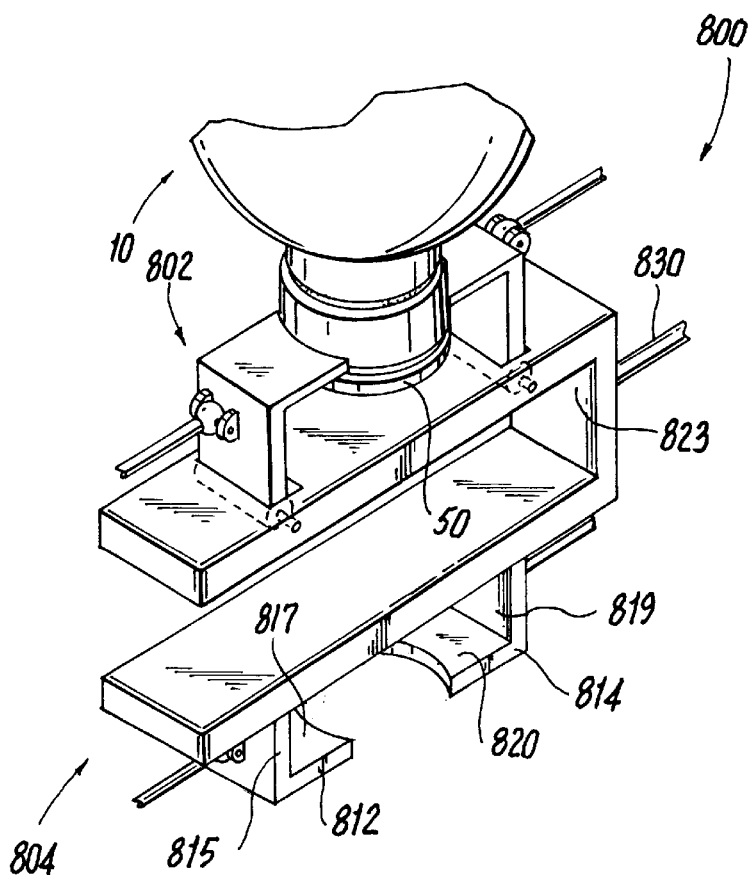
FIG. 9b is a perspective view of the exemplary safety cap removal device of FIG. 9 having another gripping member.

In another embodiment, shown in FIG. 9b, a second gripping member 804 is provided. Similarly, the second gripping member 804 has first and second spaced elements 812, 814 that are movable relative to one another and are part of the same automated device as the first gripping member 802. Each of the first and second elements 812, 814 has a first end 815 that is coupled to a base 817 and an opposing second end 819 that includes a flange 820. In the illustrated embodiment, the flange 820 is bent at a 90° angle relative to the other portion of the element.

The two bases 810, 817 are connected to one another by a wall 823 and the shaft 830 extends outwardly from the wall 823. The shaft 830 is part of the automated device that is configured to rotate the first and second gripping members 802, 804. The rotation of the first and second gripping members 802, 804 permits the first and second gripping members 802, 804 to be inverted and assume each other's position. This permits one cap 50 to be dropped by one of the gripping members 802, 804, while the other of the gripping members 802, 804 engages a new vial 10.

Each of the cap removal mechanisms provides an effective, yet simple method of removing the safety cap 50 in a just-in-time for use manner. Furthermore, the mechanism is coupled to the detector that acts as a safety feature for detecting whether the vial does not include a safety cap and therefore should be rejected and not used. The lack of a safety cap on the vial can indicate the occurrence of one or more events, including that the safety cap has previously been removed and some or all of the medication in the vial has been used; that the safety cap was not properly attached and has become dislodged; and that the vial has been tampered with, etc. The above-described safety feature is incorporated into the system so that it likewise operates in a just-in-time for use manner.

Figure 10:
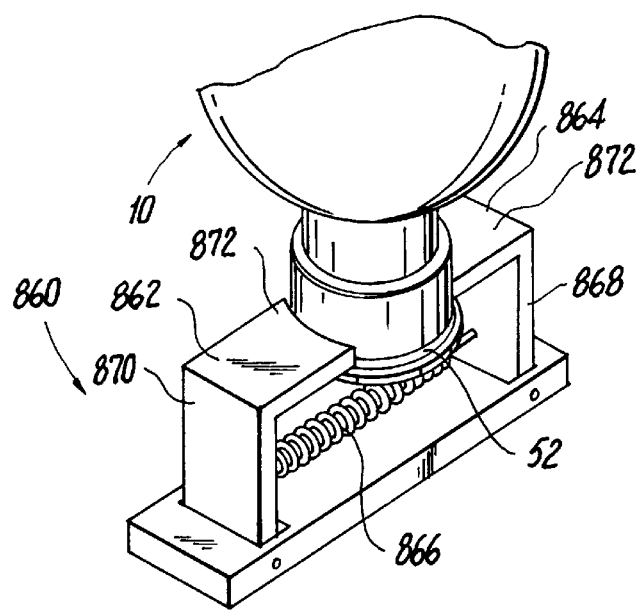
FIG. 10 is a perspective view of an exemplary safety cap removal device according to yet another embodiment.

FIG. 10 is a side elevational view of an exemplary embodiment. In this embodiment, an exemplary cap removal mechanism 860 is generally indicated. The cap removal mechanism 860 includes first and second fingers 862, 864 that are biased, e.g., spring-loaded. A spring 866 extends between the first and second fingers 862, 864 at lower ends 868 thereof. At an upper end 870 of each of the first and second fingers 862, 864, a flange 872 is formed. The flanges 872 inwardly face one another. The first and second fingers 862, 864 are slightly offset from one another. Because the first and second fingers 862, 864 are spring loaded relative to one another, various sized vials 10 can be accommodated between the first and second fingers 862, 864. For example, when larger sized vials 10 are disposed between the first and second fingers 862, 864, the first and second fingers 862, 864 flex outwardly to accommodate the size the of the vial 10.

The automated device 300 of FIG. 2 lowers the vial 10 between the first and second fingers 862, 864. As the vial 10 is lowered between the first and seconds fingers 862, 864, the biasing force causes the first and second fingers 862, 864 to engage the bottom underneath section 52 of the safety cap 50. The automated device 300 (FIG. 2) then moves the vial 10 upwards while the flanges 872 engage the bottom underneath section 52. The first and second fingers 862, 864 can employ a sensor(s) (not shown) for signaling when the flanges 872 are in engagement with the bottom underneath section 52. In this embodiment, once the sensor(s) detects and signals the control unit, the automated device 300 is instructed by the control unit to move the vial upward. The safety cap 50 is leveraged off of the vial and falls into the chute 500 (FIG. 7). Sensor 510 (FIG. 7) is used to detect the removal of the safety cap 50 and operates in the same manner in that if the safety cap 50 is not detected, the cap removal process is repeated several times.

Figure 11:
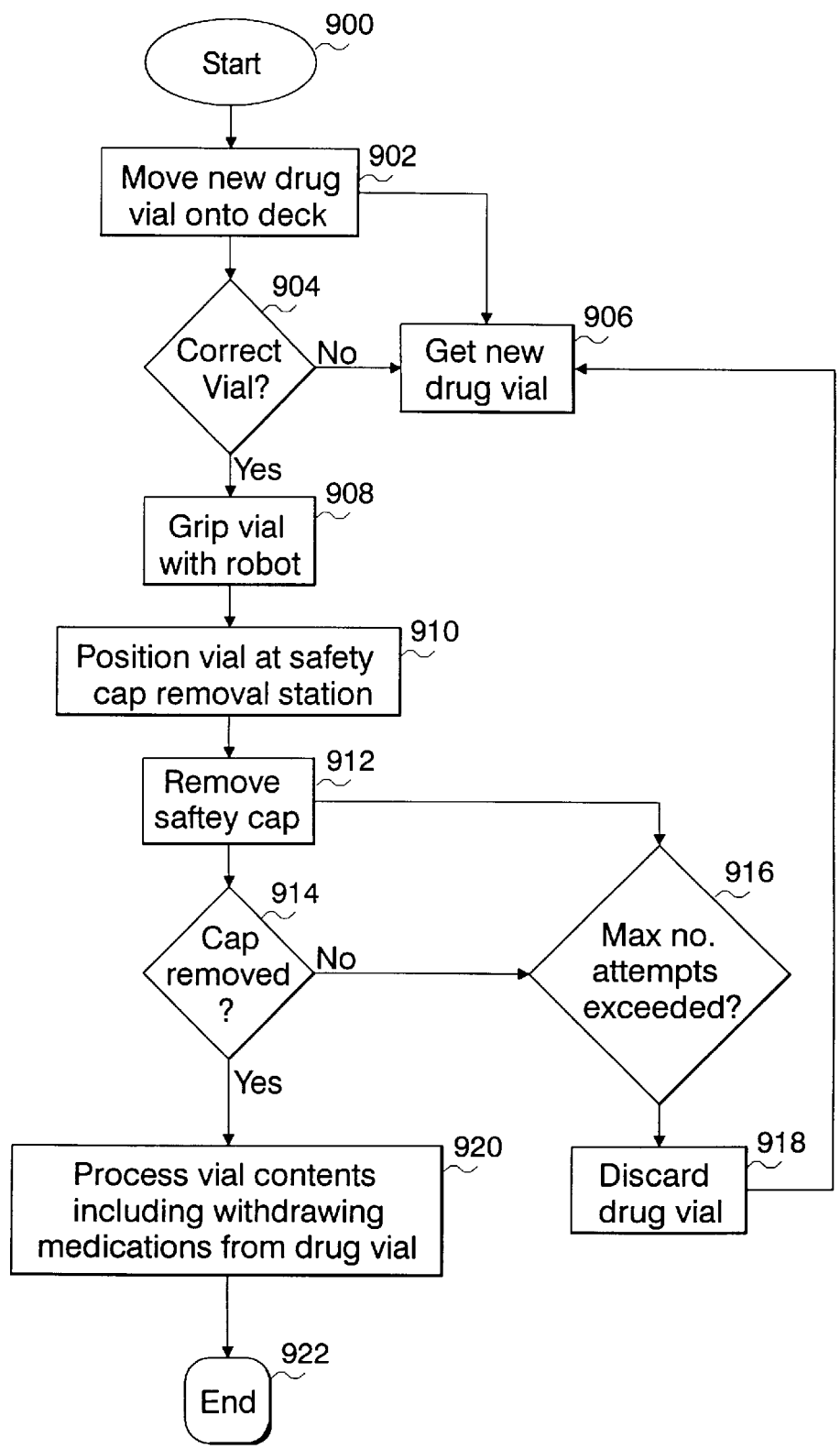
FIG. 11 is a process flow diagram illustrating a method for just-in-time removal of a safety cap from a drug vial.

FIG. 11 is a process flow diagram illustrating a method for just-in-time removal of a safety cap from a drug vial. At step 900, the process is initiated. At step 902, one drug vial 10 (FIG. 1) is moved onto a deck of the automated medication preparation system 100 (FIG. 2). It is then determined at step 904 whether the drug vial 10 is a proper vial (i.e., contains the correct medicament). This can be done using a reader (i.e., bar code scanner) as previously mentioned. If the vial 10 is not correct, the drug vial 10 is not used and a new drug vial is obtained, as shown in step 906. If the drug vial 10 is the proper drug vial, the vial is gripped by automated device 300 (FIG. 3), or the like, at step 908. At step 910, the gripped drug vial 10 is then positioned at the safety cap removal station 160 (FIG. 2).

The safety cap is then removed at step 912. At step 914, it is determined whether the safety cap is removed or not. If it is determined that the safety cap has not been removed, the cap removal process is repeated a predetermined number of times, as shown in step 916. If after repeating the cap removal process the predetermined number of times, the safety cap has not been detected as being removed, the drug vial is discarded, step 918, and a new drug vial is obtained (step 906). If the safety cap is removed, the vial contents are processed and this includes withdrawing medication from the drug vial, as shown at step 920. This completes the process (step 922). After, preparing one medication, the process can be repeated to prepare additional medication preparations or the process can be started over to prepare a new medication preparation.

It will be appreciated by persons skilled in the art that the present invention is not limited to the embodiments described thus far with reference to the accompanying drawing. Rather the present invention is limited only by the following claims.

What is claimed:

1. An automated safety cap removal mechanism for an automated medication preparation system, the mechanism comprising:

an automated gripping means for securely holding and transporting a vial containing the medication to and from a first station; and a cap removal means for removing a safety cap of the vial in a just-in-time for use manner, the cap removal device being located at the first station.

2. An automated safety cap removal mechanism for an automated medication preparation system, the mechanism comprising:

an automated gripping means for securely holding and transporting a vial containing the medication to and from a first station; and a cap removal means for removing a safety cap of the vial in a just-in-time for use manner, the cap removal means including a support member and a pivotable member coupled to the support member, the pivotable member being biased in a first direction such that when the automated gripping means delivers the vial to the first station, the pivotable member engages the safety cap which is then removed from the vial by moving the vial in a second direction as it is held by the automated gripping means.

3. The automated safety cap removal mechanism of claim 2, wherein the automated gripping means is a robotic device having first and second positionable gripping arms that are spaced apart from one another in a first position and are moved toward one another in a second position so as to securely capture and hold the vial between the first and second gripping arms.

4. The automated safety cap removal mechanism of claim 3, wherein at least one of the first and second gripping arms has an arcuate recess to receive a body of the vial.

5. The automated safety cap removal mechanism of claim 3, wherein the first and second gripping arms are rotatable so as to cause the vial to be inverted.

6. The automated safety cap removal mechanism of claim 2, wherein the pivotable member is spring biased in the first direction facing the vial that is securely held by the automated gripping means.

7. The automated safety cap removal mechanism of claim 2, wherein the pivotable member includes a flange that extends outwardly from a body of the pivotable member and is angled relative thereto, the flange being configured to seat against and apply a biasing force against the safety cap.

8. The automated safety cap removal mechanism of claim 2, wherein the second direction is a direction away from the pivotable member, wherein the pivotable member prevents movement of the safety cap in the second direction resulting in the safety cap being dislodged from the vial.

9. The automated safety cap removal mechanism of claim 2, wherein the support member has a pair of spaced arms, the pivotable member being held pivotably between the spaced arms.

10. The automated safety cap removal mechanism of claim 2, further including a chute disposed beneath the safety cap for receiving the safety cap after it has been removed from the vial.

11. The automated safety cap removal mechanism of claim 2, further including a detector for sensing the removal of the safety cap from the vial.

12. The automated safety cap removal mechanism of claim 11, further including a chute disposed beneath the safety cap for receiving the safety cap after it has been removed from the vial and wherein the detector is positioned in the chute.

13. The automated safety cap removal mechanism of claim 11, wherein the detector is in communication with a control unit that also communicates with the automated gripping means for moving the automated gripping means to select locations, the detector generating a detection signal upon sensing the safety cap, the detection signal instructing the control unit to proceed with moving the decapped vial to one of a next station and a next operation.

14. The automated safety cap removal mechanism of claim 13, wherein the control unit is programmed so that the vial is not advanced to one of the next station and the next operation unless the detection signal is received, and wherein the control unit instructs the automated gripping means to attempt one or more additional times to remove the safety cap if the detection signal is not received.

15. The automated safety cap removal mechanism of claim 11, wherein the detector is a sensor for detecting the safety cap as it falls from the vial.

16. An automated safety cap removal mechanism for an automated medication preparation system, the mechanism comprising:

an automated gripping means for securely holding and transporting a vial containing the medication to and from a first station; and a cap removal means for removing a safety cap of the vial in a just-in-time for use manner, the cap removal device including a wedge element for reception between the safety cap and a body of the vial such that when the automated gripping means delivers the vial to the first station, the wedge element is received between the safety cap and the vial body, the safety cap is then removed from the vial by moving the vial in a second direction as it is held by the automated gripping means.

17. The automated safety cap removal mechanism of claim 16, wherein the automated gripping means is a robotic device having first and second positionable gripping arms that are spaced apart from one another in a first position and are moved toward one another in a second position so as to securely capture and hold the vial between the first and second gripping arms.

18. The automated safety cap removal mechanism of claim 17, wherein the first and second gripping arms are rotatable so as to cause the vial to be inverted.

19. The automated safety cap removal mechanism of claim 16, wherein the wedge element is a tapered member that terminates in an edge that is received between the safety cap and the vial body.

20. The automated safety cap removal mechanism of claim 16, wherein the second direction is a direction away from the wedge element, wherein the wedge element prevents movement of the safety cap in the second direction resulting in the safety cap being dislodged from the vial.

21. The automated safety cap removal mechanism of claim 16, further including a chute disposed beneath the safety cap for receiving the safety cap after it has been removed from the vial.

22. The automated safety cap removal mechanism of claim 16, further including a detector for sensing the removal of the safety cap from the vial.

23. The automated safety cap removal mechanism of claim 22, further including a chute disposed beneath the safety cap for receiving the safety cap after it has been removed from the vial and wherein the detector is positioned in the chute.

24. The automated safety cap removal mechanism of claim 22, wherein the detector is in communication with a control unit that also communicates with the automated gripping means for moving the automated gripping means to select locations, the detector generating a detection signal upon sensing the safety cap, the detection signal instructing the control unit to proceed with moving the decapped vial to one of a next station and a next operation.

25. The automated safety cap removal mechanism of claim 24, wherein the control unit is programmed so that the vial is not advanced to one of the next station and the next operation unless the detection signal is received, and wherein the control unit instructs the automated gripping means to attempt one or more additional times to remove the safety cap if the detection signal is not received.

26. The automated safety cap removal mechanism of claim 22, wherein the detector is a sensor for detecting the safety cap as it falls from the vial.

27. An automated safety cap removal mechanism for an automated medication preparation system, the mechanism comprising:

an automated gripping means for securely holding and transporting a vial containing the medication to and from a first station; and a cap removal means for removing a safety cap of the vial in a just-in-time for use manner, the cap removal device including a rotatable member having first and second gripping sections, each of the first and second gripping sections having openable and closeable decapper elements that are controlled by a control unit, the safety cap being removed by disposing the safety cap between the opened decapper elements which are then closed prior to moving the vial in a second direction as the safety cap is gripped by the decapper elements.

28. The automated safety cap removal mechanism of claim 27, wherein each decapper element has an inwardly directed flange formed at one end for engaging the safety cap when the decapper elements are closed.

29. The automated safety cap removal mechanism of claim 27, wherein the openable and closeable decapper elements of each of the first and second gripping sections are coupled to a base section, the base section catching the safety cap after it has been removed from the vial.

30. The automated safety cap removal mechanism of claim 27, wherein the automated gripping means is a robotic device having first and second positionable gripping arms that are spaced apart from one another in a first position and are moved toward one another in a second position so as to securely capture and hold the vial between the first and second gripping arms.

31. The automated safety cap removal mechanism of claim 27, wherein the second direction is a direction away from the rotatable member, wherein the decapper elements prevent movement of the safety cap in the second direction resulting in the safety cap being dislodged from the vial.

32. The automated safety cap removal mechanism of claim 27, further including a chute disposed beneath the safety cap for receiving the safety cap after it has been removed from the vial.

33. The automated safety cap removal mechanism of claim 27, further including a detector for sensing the removal of the safety cap from the vial.

34. The automated safety cap removal mechanism of claim 33, further including a chute disposed beneath the safety cap for receiving the safety cap after it has been removed from the vial and wherein the detector is positioned in the chute.

35. The automated safety cap removal mechanism of claim 33, wherein the detector is in communication with a control unit that also communicates with the automated gripping means for moving the automated gripping means to select locations, the detector generating a detection signal upon sensing the safety cap, the detection signal instructing the control unit to proceed with moving the decapped vial to one of a next station and a next operation.

36. The automated safety cap removal mechanism of claim 35, wherein the control unit is programmed so that the vial is not advanced to one of the next station and the next operation unless the detection signal is received, and wherein the control unit instructs the automated gripping means to attempt one or more additional times to remove the safety cap if the detection signal is not received.

37. The automated safety cap removal mechanism of claim 33, wherein the detector is a sensor for detecting the safety cap as it falls from the vial.

38. An automated safety cap removal mechanism for an automated medication preparation system, the mechanism comprising:

an automated gripping means for securely holding and transporting a vial containing the medication to and from a first station; and a cap removal means for removing a safety cap of the vial in a just-in-time for use manner, the cap removal device including first and second fingers that are biased relative to one another, the safety cap being removed by disposing the safety cap between the first and second biased fingers such that a flange of each finger engages the safety cap and then moving the vial in a second direction as the safety cap is gripped by the first and second biased fingers resulting in the safety cap being removed.

39. A method for just-in-time removal of a safety cap from a drug vial, comprising the steps of:

moving the drug vial onto a deck of an automated medication preparation system, the drug vial having the safety cap affixed over an opening thereof;

gripping the drug vial against movement; and performing a step for removing the safety cap while gripping the drug vial.

40. The method of claim 39, wherein the performing step comprises prying the safety cap from the drug vial by inserting a member between the safety cap and adjacent body of the vial and moving the drug vial in a direction away from the member.

41. The method of claim 39, including the additional step of positioning the gripped drug vial at a station at which the performing step occurs.

42. The method of claim 39, including the additional step of providing a laminar air flow across the deck of the automated medication preparation system.

43. The method of claim 39, including the additional step of detecting the removal of the safety cap from the drug vial.

44. The method of claim 43, wherein the detecting step comprises:

permitting the safety cap to fall into a chute; and registering the passage of the safety cap through the chute.

45. The method of claim 44, wherein the registering step is tested to occur in accordance with instructions from a control unit.

46. The method of claim 43, including the additional step of withdrawing medication from the drug vial if the detecting step detects the removal of the safety cap.

47. The method of claim 43, including the additional step of discarding the drug vial if the detecting step fails to detect the removal of the safety cap after a predetermined number of attempts to perform the performing step.

* * * * *